United States Patent
Witer et al.

(10) Patent No.: US 6,892,568 B2
(45) Date of Patent: May 17, 2005

(54) NOISE DETECTION SYSTEM AND METHOD

(75) Inventors: Tony Witer, Anna, OH (US); Kelly Hennessy, Anna, OH (US); Chris Sullivan, Anna, OH (US)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 41 days.

(21) Appl. No.: 10/356,897

(22) Filed: Feb. 3, 2003

(65) Prior Publication Data

US 2004/0149022 A1 Aug. 5, 2004

(51) Int. Cl.[7] .............................................. G01M 17/00
(52) U.S. Cl. ........................................................ 73/116
(58) Field of Search ............................. 73/35.01, 112, 73/116, 117.2, 117.3, 118.1, 119 R, 121, 129; 340/425.5, 438; 701/29

(56) References Cited

U.S. PATENT DOCUMENTS

| | | | | |
|---|---|---|---|---|
| 3,695,098 A | | 10/1972 | Kirkland, Jr. | |
| 6,131,454 A | * | 10/2000 | Kopp et al. | 73/457 |
| 6,470,753 B2 | * | 10/2002 | Maruyama | 73/657 |
| 2002/0103595 A1 | * | 8/2002 | Kostun | 701/111 |
| 2003/0088346 A1 | * | 5/2003 | Calkins et al. | 701/29 |
| 2003/0136192 A1 | * | 7/2003 | Tu et al. | 73/587 |
| 2003/0221487 A1 | * | 12/2003 | Silvagi et al. | 73/462 |
| 2003/0233872 A1 | * | 12/2003 | Boulot | 73/146 |

* cited by examiner

*Primary Examiner*—Eric S. McCall
(74) *Attorney, Agent, or Firm*—Rankin, Hill, Porter & Clark LLP; Vincent Ciamacco

(57) ABSTRACT

A method for detecting and reducing an offensive noise in a vehicle having an engine. A noise is sensed in an area of interest of the vehicle. The area of interest contains a plurality of parts capable of generating the offensive noise. The sensed noise is analyzed to determine components of the noise. The offensive noise is determined based on the sensed noise and the determined noise components. Which one of the plurality of offensive noise generating parts is generating the offensive noise is determined. The offensive noise generating part is affected to reduce the offensive noise coming therefrom and thereby reducing the offensive noise in the area of interest of the vehicle.

13 Claims, 4 Drawing Sheets

NOISE DETECTION SYSTEM AND METHOD

BACKGROUND OF THE INVENTION

1. Field of the Invention

The present invention relates generally to a method and system for detecting, analyzing, and reducing an offensive noise in a vehicle, and more particularly to a method and system for determining a location of an offensive noise component and implementing a countermeasure to reduce or eliminate the offensive noise component.

2. Description of Related Art

An operating vehicle produces noise that is audible in the passenger compartment of the vehicle. The audible noise is comprised of a plurality of noise components of differing frequencies from a variety of different sources. The sources include the contact of the wheels to the road, the running engine, and the wind moving past the operating vehicle.

Some portions of the audible noise are desirable, and other portions of the audible noise offensive to an operator and passenger in the passenger compartment of the vehicle. The offensive noise can negatively impact the quality, enjoyment and marketability of the vehicle. Further, variation of offensive noise levels of different vehicles of the same model, and of different models of vehicles, is problematic for quality assurance purposes. Therefore, it is desirable to identify the offensive noise, find a source of the offensive noise, and reduce or eliminate the offensive noise in the passenger compartment of a vehicle.

SUMMARY OF THE INVENTION

The present invention provides a method for detecting and reducing an offensive noise in a vehicle having an engine. In the method according to the invention, a noise is sensed in an area of interest of the vehicle. The area of interest contains a plurality of parts capable of generating the offensive noise. The sensed noise is analyzed to determine components of the noise. The offensive noise is determined based on the sensed noise and the determined noise components. Which one of the plurality of offensive noise generating parts is generating the offensive noise is determined. The offensive noise generating part is affected to reduce the offensive noise coming therefrom and thereby reducing the offensive noise in the area of interest of the vehicle.

In accordance with another aspect of the invention, a method is provided for employing a noise-reducing countermeasure in a vehicle having an engine. Noise is sensed in a passenger compartment of the vehicle. The sensed noise is analyzed to determine an offensive noise component. The offensive noise component is sensed in a second area spaced from the passenger compartment. The offense noise component is sensed to determine a part that is a source of the offensive noise component. The part is scanned with a laser vibrometer to determine a location on the part from which the offensive noise component emanates. A countermeasure at or near the location on the part is determined. Implementing the countermeasure can reduce the offensive noise component of the noise sensed in the passenger compartment.

The present invention also provides a system for determining a location of an offensive noise component in a vehicle having an engine. The system includes a noise detection device that detects noise. A noise analyzer analyzes the noise to determine the offensive noise component of the noise. A sound intensity scanner scans an area of interest to determine the area of highest intensity of the offensive noise component to identify a part that generates the offensive noise component. A laser vibrometer scans the part to determine where on the part the offensive noise component emanates from. In another aspect of the invention, a countermeasure can be determined based on the location and the part. Implementing the countermeasure reduces or eliminates the offensive noise component. The system can then double check the passenger compartment to ensure that the countermeasure had the effect of reducing or eliminating the offensive noise.

BRIEF DESCRIPTION OF THE DRAWINGS

These and further features of the invention will be apparent with reference to the following description and drawings, wherein.

DETAILED DESCRIPTION OF PREFERRED EMBODIMENTS

Figure 1:
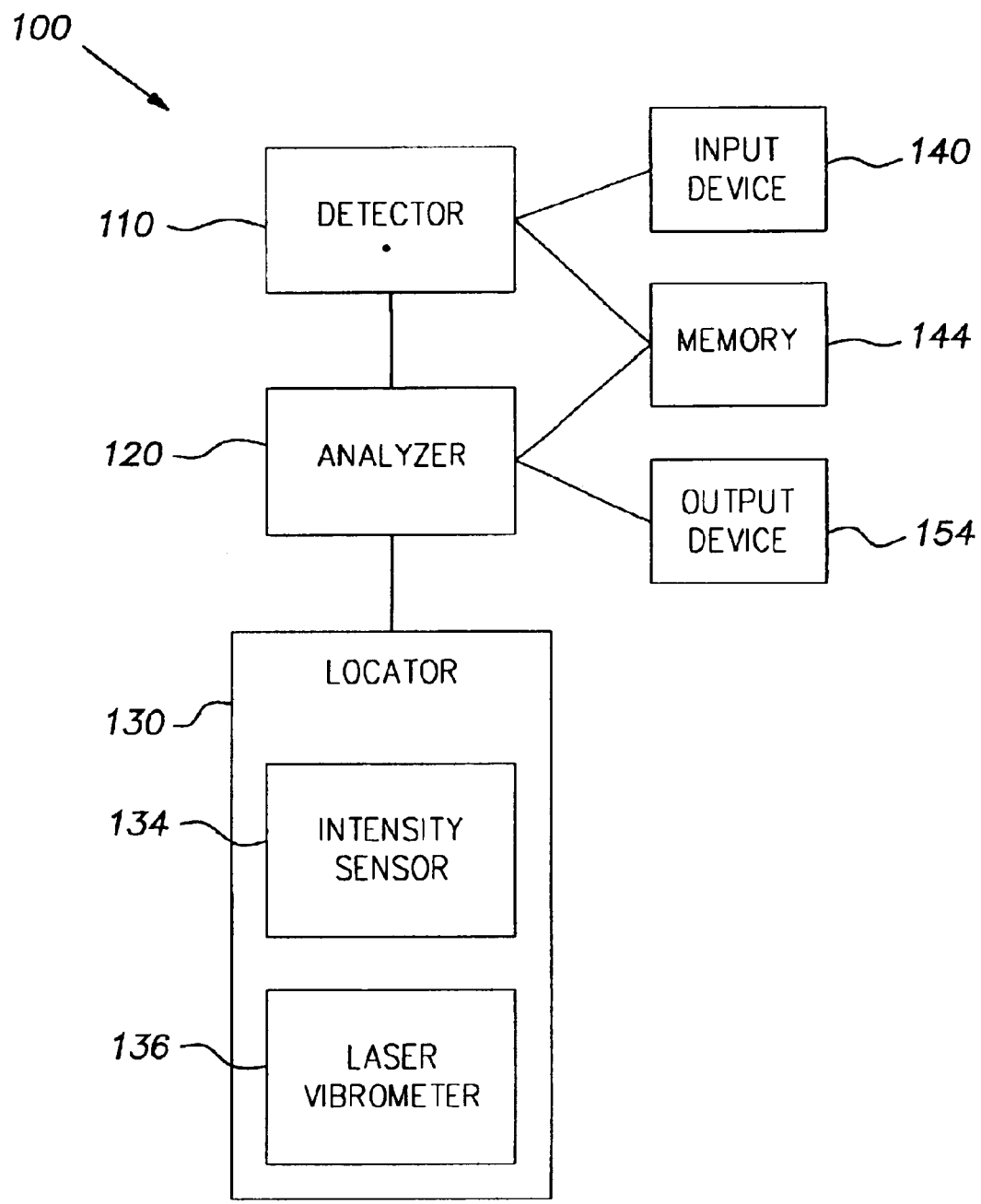
FIG. 1 is a schematic block diagram of an apparatus for use with a method according to the present invention.

A schematic block diagram of an offensive noise detection, analysis, location and reduction system 100 in accordance with the present invention is shown in FIG. 1. The system 100 is for use on a vehicle having an engine while the engine is running. The system 100 detects and analyzes noise, and a location from which the noise emanates, so that an appropriate counter-measure can be determined and implemented based on the noise emanating location.

The system 100 includes a noise detection device or detector 110, a noise analyzer 120 that communicates with the detector 110, and a noise location system or locator 130 that communicates with the analyzer 120. The locator 130 includes a noise intensity sensor 134 and a laser vibrometer 136. An input device or microphone 140 communicates with the detector 110. A memory device 144 communicates with both the detector 110 and the analyzer 120. The analyzer 120 can optionally also communicate with an output device or memory 154, if present.

The detector 110 detects ambient noise in a first area, for example a passenger compartment in the vehicle. The noise is detected with reference to variables in predetermined ranges. The variables can include engine revolutions per minute (RPM) and the volume of the passenger compartment. The range of RPM can include from idle to racing, and the range of space can be from passenger side to drivers side, and can be subdivided into front and rear seating areas, and so forth. The noise is sensed by the microphone 140, which provides input data to the detector 110.

The detector 110 communicates the input data to the analyzer 120. The analyzer 120 analyzes the noise input data to determine the components or frequencies of the noise. The analyzer 120 identifies which component is the offensive noise or frequency. Information identifying the offensive noise is communicated to the locator 130 and/or the optional memory 154. If the offensive noise information is communicated to the memory 154, the memory 154 stores the information for retrieval and later use.

When the offensive noise information is communicated to the locator 130, the sound intensity sensor 134 scans an area to determine generally the location from which the offensive noise emanates. For example, first the sound intensity sensor 134 can be set using the offensive noise information so as to detect the offensive noise from the total noise generated by the running engine. Next, the vehicle engine is run, and the sound intensity sensor 134 scans the vehicle engine compartment to determine which of the engine parts of the running engine is generating the offensive noise that was detected in the passenger compartment of the vehicle.

When the sound intensity sensor 134 determines which of the engine parts is the part generating the offensive noise, that part can be scanned with the laser vibrometer 136. Generally, the laser vibrometer 136 scans the part while the engine is running to determine a location on the part that generates the offensive noise. If possible, the part may be scanned while operated independent of the engine.

Figure 2:
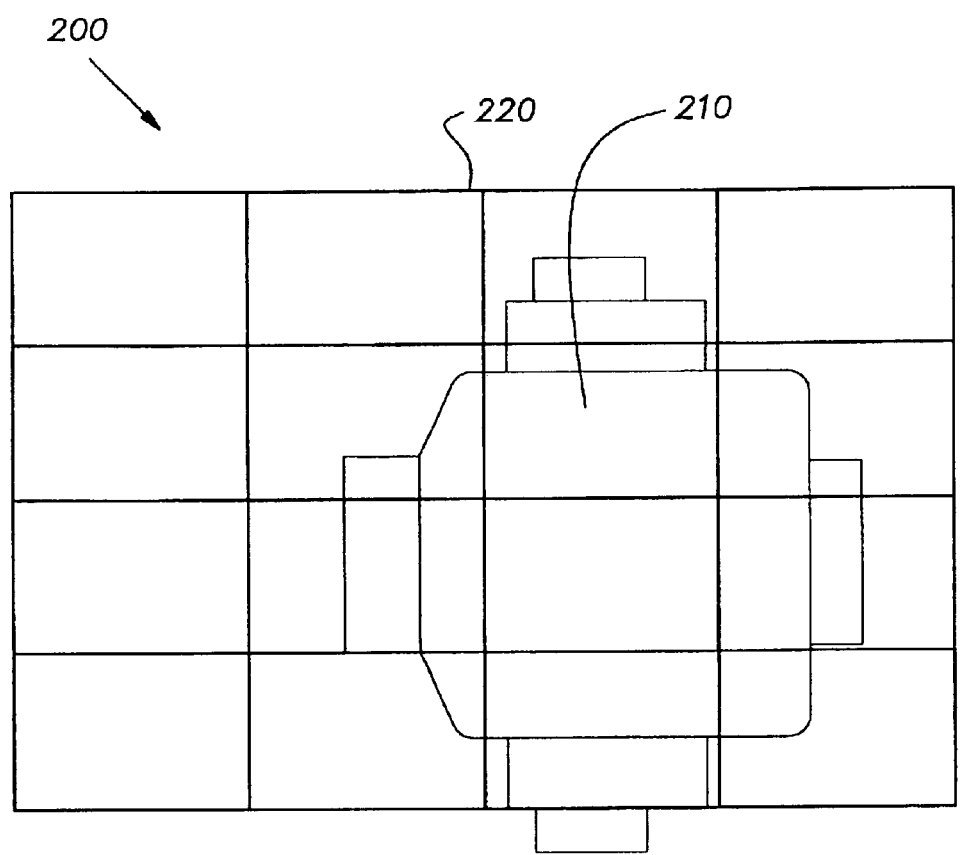
FIG. 2 is a schematic view of an exemplary part with a grid overlay of a method in accordance with the invention.

With reference to FIG. 2, a schematic illustration 200 of a method in accordance with the invention is shown. The illustration 200 includes a schematic representation of an engine part 210, which has been found via the sound intensity scanner 134, to generate the offensive noise while the engine is running. An imaginary grid 220 overlays the engine part 210. The laser vibrometer 136 scans the part 210 with reference to the grid 220 to determine or identify the specific location from which the offensive noise (hereinafter referred to as the "noise source") emanates relative to the grid 220. The noise source, as viewed by the laser vibrometer, vibrates at the offensive frequency previously identified by the sound intensity sensor 134 and/or detector 110, and will be readily apparent.

Based on the noise source or grid coordinates, an appropriate countermeasure is selected. The countermeasure can be, for example, re-engineering, or either adding material to the generation location or removing material from the noise source. For example, if the noise source is a protruding ridge of metal that vibrates during operation of the engine, the ridge may be strengthened or stiffened by adding additional metal to the ridge. Alternatively, if the ridge in this example serves no or an unimportant function, the ridge itself may be removed. Further, the shape of the ridge can be altered or the material from which the ridge is made can be replaced with a different material. The countermeasure can also be a combination of the foregoing options. The preferred countermeasures are strengthening or weakening the noise source.

After implementing the countermeasure, the detector 110 can resample the noise in the passenger compartment. The analyzer 120 analyzes the resampled noise to determine if the offensive noise is reduced or eliminated. If the offensive noise has not been reduced to a satisfactory level or eliminated by the implementation of the countermeasure, an additional or different countermeasure is applied to the generation location or the process is repeated to determine if there are additional locations generating the offensive noise during operation of the vehicle.

Figure 3:
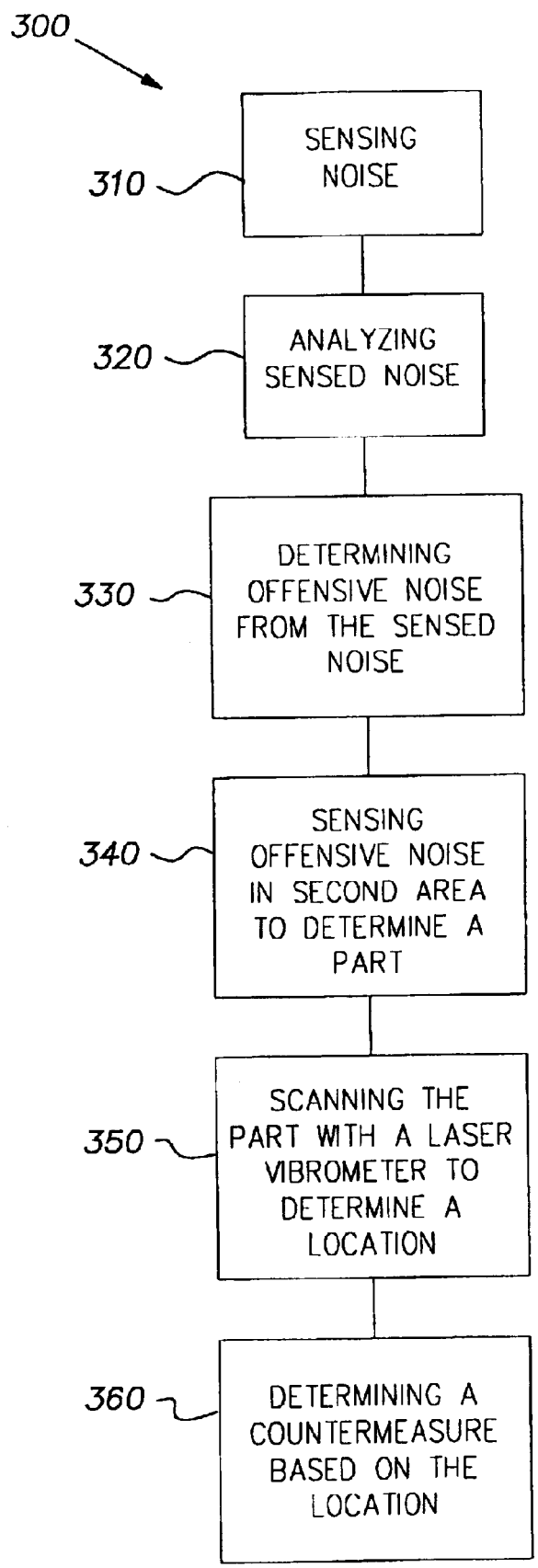
FIG. 3 is a flow chart of a method in accordance with an aspect of the invention.

With reference to FIG. 3, a flow chart 300 of the steps of a method in accordance with the present invention is shown. In block 310 a noise is sensed. This can be accomplished, for example, by using the detector 110. The sensed noise is analyzed in block 320. The analysis of block 320 determines which is the offensive noise of the sensed noise in block 330, including the frequency or frequencies constituting the offensive noise. A second area space from the first area is scanned for the offensive noise determined in block 330. The sensing in the second area determines or identifies which part is generating the offensive noise in block 340. Having identified the part in block 340, the part's surface is scanned in block 350 with a laser vibrometer to determine a location (i.e., noise source) on the part that is generating the offensive noise. A countermeasure is determined in block 360 based on the determined location (noise source) on the part.

Figure 4:
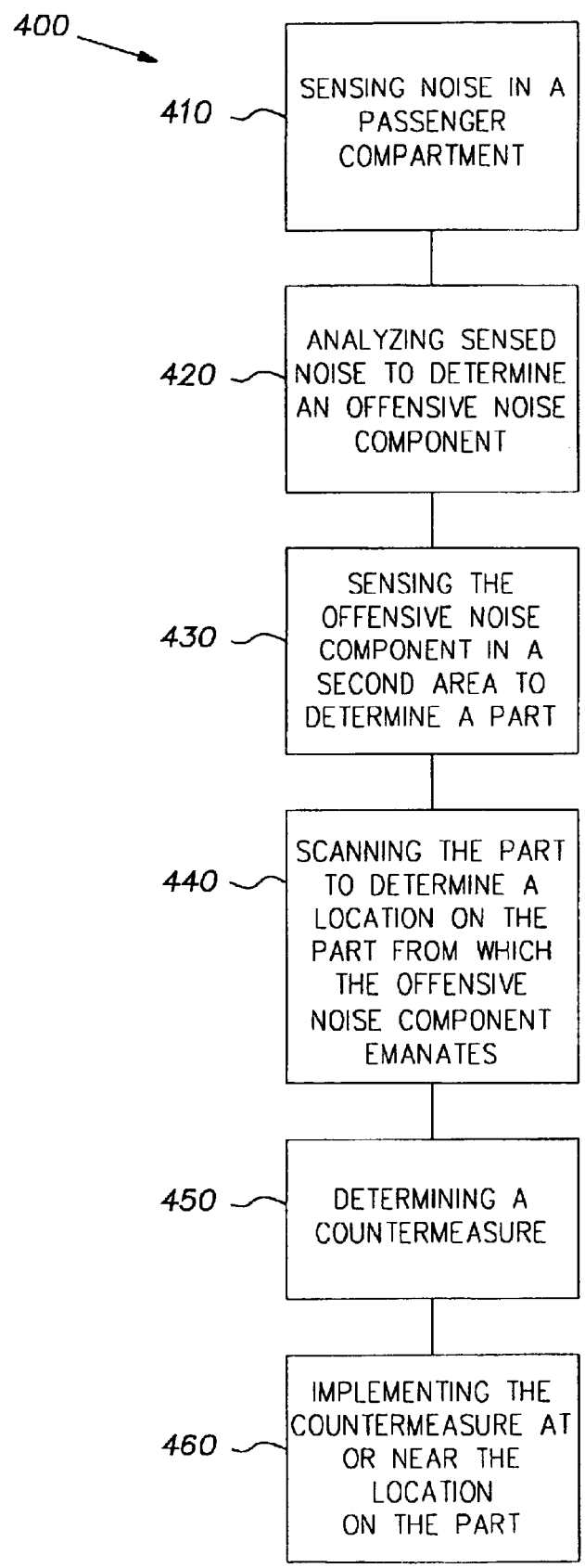
FIG. 4 is a flow chart of a method in accordance with another aspect of the invention.

With reference to FIG. 4, a flow chart 400 of the steps of a method in accordance with the present invention is shown. In block 410 a noise is sensed in a passenger compartment of a vehicle while the engine is running, that is, the vehicle is being operated. The sensed noise is analyzed in block 420 to determine or isolate the offensive noise component from the sensed noise. A sound intensity scanner senses a second area, for example, in a second area outside of or spaced from the passenger compartment to identify a part that is generating the offensive noise component, as shown in block 430. Once the part is identified, the part's surface is scanned in block 440 to determine a location (noise source) on the part, for example a portion of the part housing, from which the offensive noise component emanates. In block 450, a countermeasure is determine based on the part and/or the location of part relative to the passenger compartment, and further on the location of the noise source, which generates the offensive noise component of the noise. The countermeasure is implemented in block 460 at or near the noise source on the part so as to reduce or eliminate the offensive noise component of the sensed noise in the passenger compartment of the vehicle.

The embodiments described herein are examples of structures, systems and methods having elements corresponding to the elements of the invention recited in the claims. This written description may enable those skilled in the art to make and use embodiments having alternative elements that likewise correspond to the elements of the invention recited in the claims. The intended scope of the invention thus includes other structures, systems and methods that do not differ from the literal language of the claims, and further includes other structures, systems and methods with insubstantial differences from the literal language of the claims.

What is claimed is:

1. A method for detecting and reducing an offensive noise in a vehicle, comprising the steps of:

sensing noise in an area of interest of the vehicle, the area of interest containing a plurality of parts capable of generating the offensive noise;

analyzing the sensed noise to determine components of the noise;

determining which of the noise components is the offensive noise based on the sensed noise and the determined noise components;

determining which one of the plurality of parts is generating the offensive noise;

scanning the area of interest with a sound intensity scanner to determine an area of highest intensity of the offensive noise component; and affecting the offensive noise generating part to reduce the offensive noise coming therefrom to thereby reduce the offensive noise in the area of interest of the vehicle.

2. The method as defined in claim 1, further comprising the step of analyzing the offensive noise generating part using a noise analyzer during operation of the vehicle to identify a location on the part from which the offensive noise emanates.

3. A method for employing a noise-reducing countermeasure in a vehicle having an engine, comprising the steps of:

sensing noise in a passenger compartment of the vehicle;

analyzing the sensed noise to determine an offensive noise component of the sensed noise;

sensing the offensive noise component in a second area spaced from the passenger compartment, to determine a part that is a source of the offensive noise component;

scanning the part with a laser vibrometer to determine a location on the part from which the offensive noise component emanates; and determining a countermeasure to implement on the part to reduce the offensive noise component.

4. The method as defined claim 3, further comprising the steps of implementing the countermeasure, and re-sensing the noise in the first area to determine whether the implemented countermeasure reduced the offensive noise component in the first area.

5. The method as defined in claim 3, wherein the countermeasure is selected from the group consisting of stiffening the part at the location and weakening the part at the location.

6. The method as defined in claim 3, wherein the step of sensing noise in the passenger compartment comprises sampling the noise relative to differing variables.

7. The method as defined in claim 6, wherein the variables are selected from the group consisting of different locations in the passenger compartment and different operating speeds of the engine.

8. The method as defined in claim 7, wherein the different passenger compartment locations are grouped into front seat locations and rear seat locations and the sampling step is performed in only one of the grouped locations.

9. A system for determining a location of an offensive noise in a vehicle having an engine while the engine is running, comprising:

a noise detection device that is operable to detect noise that comprises the offensive noise;

a noise analyzer communicating with the noise detection device that is operable to analyze the detected noise to determine the offensive noise component of said detected noise;

a sound intensity scanner that is operable to scan an area of interest and determine an area of highest intensity of the offensive noise in the area of interest and thereby identifying a part of the vehicle that is a source of the offensive noise; and a laser vibrometer that is operable to scan a surface of the part to determine a location on the part from which said offensive noise emanates.

10. The system as defined in claim 9, wherein the laser vibrometer is further operable to scan in a pattern defining an imaginary grid that overlays the part so as to precisely identify the location on the part from which the offensive noise emanates.

11. A system to identify an area to which a countermeasure may be applied to reduce an offensive noise component of a noise in a vehicle having an engine, comprising:

a noise detection device that is operable to detect the noise in a passenger compartment of the vehicle;

a noise analyzer communicating with the noise detection device that is operable to analyze the detected noise to determine the offensive noise component of the detected noise;

a sound intensity scanner that is operable to scan an area of interest and determine an area of highest intensity of the offensive noise component in the area of interest and thereby identify a part that is a source of the offensive noise component; and a laser vibrometer that is operable to scan a surface of the part to determine a location on the part from which the offensive noise component emanates, so as to identify the area to which the countermeasure for reducing the offense noise component may be applied.

12. The system as defined in claim 11, wherein the laser vibrometer is further operable to scan in a pattern defining an imaginary grid that overlays the part so as to precisely identify the location from which the offensive noise component emanates.

13. The method of claim 1, including the additional step of scanning a surface of the part with a laser vibrometer to determine a location on the part from which the offensive noise component emanates.

* * * * *